United States Patent [19]

Armstrong

[11] Patent Number: 4,841,080

[45] Date of Patent: Jun. 20, 1989

[54] PROCESS FOR THE OXIDATION OF ETHYLENE TO ETHYLENE OXIDE

[75] Inventor: William D. Armstrong, Ramsey, N.J.

[73] Assignee: Scientific Design Company, Inc., Little Ferry, N.J.

[21] Appl. No.: 156,212

[22] Filed: Feb. 16, 1988

Related U.S. Application Data

[62] Division of Ser. No. 361,304, Mar. 24, 1982, Pat. No. 4,760,042.

[51] Int. Cl.$^4$ .............................................. C07D 301/3
[52] U.S. Cl. ................................... 549/536; 549/534; 549/537
[58] Field of Search ................................ 549/534, 536

[56] References Cited

U.S. PATENT DOCUMENTS 4,760,042  7/1988  Armstrong .......................... 549/534

*Primary Examiner*—Glennon H. Hollrah
*Assistant Examiner*—A. A. Owens
*Attorney, Agent, or Firm*—Kenneth H. Johnson

[57] ABSTRACT

A supported silver catalyst for the oxidation of ethylene with molecular oxygen to ethylene oxide is made by depositing silver on a support capable of selectively adsorbing alkali metals, activating the silver under conditions chosen to provide the optimum selectivity of ethylene oxide and thereafter depositing an amount of an alkali metal sufficient to increase selectivity of the silver catalyst above its alkali-free state. The catalyst most preferably employs a ceramic support having a surface area of 0.3–0.8 m$^2$/gm. The amount of alkali metal on the finished catalyst is most preferably 50–300 ppm by weight. The catalyst may also include additional promoters, such as the alkaline earth metals, preferably barium.

12 Claims, No Drawings

PROCESS FOR THE OXIDATION OF ETHYLENE TO ETHYLENE OXIDE

This application is a division of Ser. No. 361,304, filed March 24, 1982, now U.S. Pat. No. 4,760,042.

BACKGROUND OF THE INVENTION

The invention relates generally to the oxidation of ethylene to ethylene oxide over a supported silver catalyst. Such catalyst and processes are well known in the prior art. More specifically, the invention relates to an improved catalyst employing a characteristic support. The catalyst is activated in a manner intended to provide the optimum selectivity to ethylene oxide. Catalysts prepared according to the invention are further improved by post-depositing alkali metals in minor amounts on the activated silver catalyst.

Many patents show the use of supported silver catalysts for the oxidation of ethylene to ethylene oxide. For many years, promoting metals have been added to further improve performance, and in particular the alkali metals. The art in this field has been very extensive as may be seen in a lengthy review of these patents given in G.B. 2,043,481A. Such disclosures have been somewhat inconsistent in their teachings, as can be seen by comparing U.S. Pat. No. 2,238,474 in which sodium and lithium hydroxides were suggested as promoters and potassium and cesium were shown to act as poisons with U.S. Pat. No. 2,671,764 where rubidium and cesium sulfates were suggested as promoting compounds.

Although alkali metals were suggested generally in the earlier disclosures, more recent workers in the field have considered potassium, rubidium, and cesium as the preferred alkali metals. For example, see the series of patents to Nielson, et al. in which these materials were used in small amounts co-deposited with the silver, i.e. U.S. Pat. Nos. 3,962,136, 4,010,115, and 4,012,425. Still more recently the art has emphasized obtaining synergistic combinations of the alkali metals. For example see G.B. 2,043,481A cited above, and U.S. Pat. Nos. 4,212,772 or 4,226,782. In addition to their use in the preparation of fresh catalysts, the alkali metals have been used to rejuvenate used catalysts, as shown in U.S. Pat. No. 4,033,903 and a group of patents assigned to Hoechst, A.G. including U.S. Pat. Nos. 4,123,385 4,177,169 and 4,186,106. The art teaches that the alkali metals may be deposited either before the silver is placed on the support (pre-deposited), at the same time the silver is deposited (co-deposited), or subsequent to deposition of the silver (post-deposited). Examples of these techniques are given in U.S. 4,207,210 (pre-deposited), and the group of Nielson, et al. patents mentioned previously (co-deposited), and in U.S. Pat. Nos. 4,066,575 and 4,248,740, and G.B. 2,045,636A (post-deposited).

The useful amount of alkali metal was suggested to be quite wide in the older art. It was often indicated that large quantities, e.g. up to several percent of an alkali metal could be used. More recently, the art generally has taught that small quantities of alkali metals produce the optimum effect no matter when the silver and the alkali metals were deposited, although Kilty in U.S. Pat. No. 4,207,210 related the optimum amount to the surface area of the support. The art generally teaches that the optimum will be found in relatively low quantities, typically about 50 to 500 ppm by weight.

While the art generally teaches that alkali metals can be post-deposited (i.e. after the silver particles have been activated), it will be seen upon close study that either special methods are required to prepare a silver catalyst which can be promoted by alkali metals, or the catalysts must be deactivated through use or by artificial aging ("stabilization"). Otherwise, the art teaches that freshly made catalysts are not susceptable to promotion by alkali metals or rapidly lose what promotional effect is achieved. See for example, U.S. Pat. No. 4,033,903 which states that freshly prepared catalysts should be "stabilized" (that is, reduced in activity) through use or by heat treating, after which a much larger improvement in selectively can be achieved by deposition of potassium, rubidium, or cesium. In Example II it is shown that a catalyst activated at 200° C. for 18 hours has essentially no response to the post-deposition of cesium. In U.S. Pat. No. 4,278,562 the same point is made and illustrated in comparative example 1. Example VII of British Pat. No. 1,413,251 teaches that post-deposition of potassium on a freshly prepared silver catalyst was inferior to the coincidental deposition of potassium with the silver. See also the patents issued to Hoechst A.G., which relate to the reactivation of used silver catalysts such as U.S. Pat Nos. 4,123,385, 4,186,106, and 4,177,169.

Patents which teach the successful promotion of freshly prepared silver catalysts by post-deposition of alkali metals include U.S. Pat. No. 4,066,575 where the silver is activated by heating in an inert atmosphere prior to deposition of an alkali metal. Example VII shows that activation of the silver in air provides a catalyst which shows little or no response to the post-deposition of cesium, while activation of the silver in nitrogen produces a catalyst which is significantly promoted by cesium. In U.S. Pat. No. 4,248,740 promotion by post-deposition of an alkali metal was achieved by heating only to temperatures of 50° to 200° C., followed by a washing with water or alcohol to provide a catalyst which can be promoted. Activation at temperatures above 200° C. in air was shown in comparative Examples 2 and 3 to be clearly inferior. Published British patent application GB 2,045,636A also shows that activation at low temperatures produces a catalyst which can be promoted by post-deposition of an alkali metal, while Example 9 teaches that higher temperature activation in air produces a catalyst which is not promotable by post-deposition.

It has now been discovered that, contrary to the teachings of the prior art, that a silver catalyst can be successfully post-deposited with an alkali metal to provide improved selectivity, which is not merely a transient improvement, but is retained for a long period of operation. This result is achieved by proper selection of the catalyst support, activating the silver under controlled conditions, and post-depositing a small amount of an alkali metal in the manner disclosed hereinafter.

SUMMARY OF THE INVENTION

A supported silver catalyst for the oxidation of ethylene to ethylene oxide is made by impregnating a support comprising alumina, silica, silica-alumina, or combinations thereof and having a surface area of about 0.05–1.5 $m^2/gm$ and characterized by having the ability to selectively adsorb (as later defined) an alkali metal with a solution of an organic silver salt, then activating said impregnated support in the presence of molecular oxygen at a maximum temperature not exceeding 500° C.

for a sufficient time to produce an active fresh catalyst having an average silver particle size of about 0.2–1.0 microns, and thereafter post-depositing on the activated silvered support an amount of 10–1000 wt. ppm based on the finished catalyst of at least one alkali metal selected from the group consisting of Cs, K, and Rb. The post-deposition of an alkali metal on a silver catalyst activated according to the invention increases the selectivity of the freshly-activated silver catalyst for the oxidation of ethylene to ethylene oxide and does not require the intentional degradation of performance of the fresh catalyst by a high temperature treatment taught by the prior art. The catalyst may also contain other promoters, such as the alkaline earth metals preferably barium.

The finished catalyst will contain 5–20 wt % silver and 10–1000 wt ppm of an alkali metal(s), preferably 10–18 wt % silver and 25–500 wt ppm alkali metal(s), most preferably 12–15 wt % silver and 50–300 wt ppm alkali metal(s). The support preferably is an alumina containing up to about 15 wt % silica having a surface area 0.1–1.0 $m^2/gm$, most preferably 0.3–0.8 $m^2/gm$.

The organic salt is preferably at least one silver carboxylate selected from the group consisting of silver acetate, silver oxalate, silver citrate, silver lactate and silver benzoate, preferably silver lactate.

It is characteristic of the support that it is capable of selectively adsorbing alkali metals from solution, by which is meant the amount of alkali metal actually found on the support is greater than the amount which would be expected from the concentration and amount of the solution absorbed by the support. This ability to selectively adsorb excess alkali metals is believed to be related to their promotional effect on the selectivity of the silver particles to oxidize ethylene to ethylene oxide. The total amount of alkali metal on the finished catalyst may be adjusted by regulating the amount of alkali metal in the impregnating solution or by absorbing an excess of alkali metal from a more concentrated solution and then washing off excess with a 1–3 carbon alkanol.

The catalyst of the invention may be employed at oxidizing conditions typical of the art to prepare ethylene oxide by the vapor-phase oxidation of ethylene with improved results.

DESCRIPTION OF THE PREFERRED EMBODIMENTS

Catalyst Composition and Preparation

Catalysts prepared in accordance with this invention contain about 5–20% by weight of silver, expressed as metal, deposited upon the surface of and throughout the pores of a porous refractory support. Silver contents higher than 20% by weight of total catalyst are effective, but result in catalysts which are unnecessarily expensive. Silver contents, expressed as metal, of 10–18% based on weight of total catalyst are preferred, while silver contents of 12–15% are especially preferred.

The nature of the porous refractory support is believed to be critical to the process of this invention. Catalysts maybe made with supports comprising alumina, silica, silica-alumina or combinations thereto. Preferred supports are those containing principally alpha-alumina, particularly those containing up to about 15 wt % silica. Especially preferred supports have a porosity of about 0.1–1.0 cc/gm and preferably about 0.3–0.8 cc/gm. Preferred supports also have a relatively low surface area, that is about 0.05–1.5 $m^2/gm$, preferably 0.1–1.0 $m^2/gm$, especially 0.3–0.8 $m^2/gm$. Such surface areas are determined by the BET method [J. Am. Chem. Soc. 60, 309–16 (1938)]. Porosities are determined by the mercury porosimeter method; see Drake and Ritter, "Ind. Eng. Chem. Anal. Ed.," 17, 787 (1945). Pore diameters and pore diameter distributions are determined from the surface area measurements and the apparent porosity measurements.

It is characteristic of the catalyst of the invention that the support be capable of selectively adsorbing alkali metals, particularly potassium, rubidium, and cesium from solutions of those metals. The mechanism by which this is accomplished is not clear, but may involve ion-exchange with other metal ions found on the support. In this regard, it is of interest to note that published British patent application GB 2,043,481A teaches against the use of supports which contain ions exchangeable with the alkali metals (page 12, line 50). However, it has been found that the promotional effect of the alkali metals is enhanced when the support can selectively adsorb alkali metal ions. By this is meant the deposition of greater amounts of alkali metals than would be predicted by calculation from the amount and concentration of the solution absorbed by the support. It may be that the additional alkali metal ions are selectively deposited on sites where their effect is more important since it can be shown that the same amount of an alkali metal provides a different response with supports on which it is selectively adsorbed, compared with those supports lacking that character. For catalysts of the invention, the support should demonstrate its ability to selectively adsorb alkali metals by being able to adsorb more than that calculated to be present when the support has been immersed in a solution containing a known amount of an alkali metal.

Supports having preferred characteristics are available from commercial sources. Illustrative support materials commercially available include the following examples.

| Designation | SA-5552[1] | SA-5551[1] | CBO-6576[2] | SA-3235[1] |
|---|---|---|---|---|
| Alumina, wt % | 93.1 | 99.3 | 97.1 | 80.3 |
| Silica, wt % | 5.6 | 0.3 | 2.5 | 17.9 |
| Apparent porosity, % | 51–57 | 41–46 | 52.6 | 65 |
| % of pores with diam. in range of (in microns): | | | | |
| <1 | 5 | 5 | 10 | 1 |
| 1–10 | 87 | 87 | 70 | 27 |
| 10–100 | 8 | 8 | 20 | 22 |
| >100 | — | — | — | 50 |
| Surface area, sq. meters/gm | 0.3–0.37 | 0.15–0.35 | 0.2–0.35 | 2–10 |
| Pore volume, cc/gm | 0.31 | 0.25 | 0.28 | 0.61 |
| % selective absorption[3] | 88 | 91 | 56 | 79 |

[1] Norton Company
[2] Carborundum Company
[3] Based on support immersed in a 700 wt ppm solution of cesium as cesium acetate in 90% ethanol - 10% water for 2 hours. See note (1) in TABLE V.

For use in commercial ethylene oxide production applications, the supports are desirably formed into regularly shaped pellets, spheres, rings, etc. Desirably, the support particles used have "equivalent diameters" in the range from 3–10 mm. and preferably in the range of 4–8 mm, which are usually compatible with the internal diameter of the tubes in which the catalyst is placed. "Equivalent diameter" is the diameter of a sphere having the same external surface (i.e. neglecting surface within the pores of the particle) to volume ratio as the support particles being employed.

The silver is added to the support by immersion of the support into a liquid containing a compound or complex of silver, thereby enabling the silver-containing liquid to penetrate by absorption and/or capillary action into the pores of the support. A single immersion or a series of immersions, with or without intermediate drying, may be used. The concentration of the compound or complex of silver in the liquid will, in large measure, determine the silver content of the finished catalyst. To obtain catalysts having silver contents within the preferred range, suitable impregnating solutions will generally contain from 5-50 wt % of silver, expressed as metal, but supplied as silver compounds or complexes. The exact concentrations employed, of course, will depend upon, among other factors, the desired silver content, upon the nature of the support, and upon the viscosity of the liquid.

The impregnating medium is a liquid containing a compound or complex of silver, which is intended to encompass solutions and complexes of silver salts, both aqueous and non-aqueous, as well as molten silver salts, with or without additional diluents.

A common, suitable and readily prepared form of liquid containing a compound or complex of silver suitable for use in this invention is a molten silver salt of an organic acid, either alone or in combination with excess organic acid. For example, one may employ silver carboxylates or hydroxy-substituted carboxylate anions. Salts of hydroxy-substituted carboxylic acids and of dibasic acids are especially preferred. To enable relatively high silver levels on catalyst to be developed with a minimal number of immersions, anions containing more than 12 carbon atoms are generally not as desirable as those containing 12 carbon atoms or less. It is preferred to avoid carboxylate anions containing halo and/or sulfur substituents. Accordingly, illustrative of the especially preferred silver salts would be silver acetate, silver oxalate, silver citrate, silver lactate, silver benzoate, etc. Silver complexes such as the acetylacetonate or like complexes of silver with an organic moiety may also be used. Aqueous solutions of inorganic silver compounds such as silver nitrate and ammoniacal silver carbonate can be employed. Such solutions preferably also contain an organic compound such as the acids mentioned above, alkyl amines such as alkyl diamines and ethanolamine, and the like.

As indicated, the silver is deposited upon the support by immersion of the support into a liquid containing a compound or complex of silver until the solution has been absorbed into the pores of the support. Typical immersion times of from 1 to 60 minutes at temperatures of from 30° to 120° C. will usually suffice to achieve silver contents of as high as 10-25 wt %, as silver, with preferred systems wherein molten silver carboxylate salts with molten excess carboxylic acid, containing the order of 30 to 60% silver, expressed as metal, are used.

If aqueous solutions are employed, substantial vaporization of water should be avoided. Thus, the contacting is preferably conducted at super-atmospheric pressures if immersion temperatures are to exceed 95°-100° C., while atmospheric pressure is adequate if contacting temperature is to be in the range from ambient to about 95° C.

In addition to the silver compounds or complex, the liquid in which the support is immersed can advantageously contain other ingredients, such as alkaline earth metal promoters e.g. barium. They are advantageously incorporated in this step by adding to the liquid a salt of the promoter metal which is soluble in the liquid in an amount sufficient to provide the desired promoter metal content in the finished catalyst. This may be about 10-10,000 ppm by weight of barium or other alkaline earth metal, preferably about 25-5000 ppm by weight, most preferably about 50-1,000 ppm by weight. The anion associated with the promoter metal is not critical and the same or similar anions as those mentioned in connection with the silver compound or complex can be employed.

Additionally, because it is desired to maintain the silver in an oxidized state during this step, additives are frequently employed. Among the additives useful for this purpose is hydrogen peroxide.

Avoidance of premature silver deposition, as well as enhancement of the ability of the silver compound or complex to permeate the support, is provided if the silver salt solution is maintained in an acid state, preferably by incorporation of free carboxylic acid, preferably that corresponding to the anion of the silver salt. Such liquids are readily made, for example, by admixing silver oxide with a carboxylic acid such as lactic acid and heating and causing the oxide to react with the acid to form the silver carboxylate, dissolved in excess carboxylic acid, liberating by-product water which need not be removed from the liquid.

Following such a procedure, and assuming that it is desired to employ silver lactate as the silver salt and to incorporate barium (supplied as barium acetate) as a promoter, a typically suitable liquid, after reaction of the silver oxide with lactic acid, would contain:

| Component | Wt % |
| --- | --- |
| Silver lactate | From 55 to 73 |
| Lactic acid | From 15 to 45 |
| Barium acetate | From 0.05 to 0.30 |
| Hydrogen peroxide (100% basis) | From 0 to 0.5 |
| Water | From 0 to 20 |

Liquids of the concentrations set forth above will readily provide finished catalysts having silver contents, expressed as metal, of from 8% to 15% based on weight of total catalyst and barium contents within the prefered range of from 100 to 500 ppm, in a single immersion.

Following impregnation, the support is separated from any non-absorbed solution. Various means might be employed. Typically, the support is placed in a perforated container and lowered into a vessel containing the solution. The container is removed from the vessel and surplus solution is allowed to drain freely for 3 to 5 minutes or longer.

After the silver compound or complex has been applied to the support, the catalyst is activated by heating the impregnated particles to a sufficient temperature to decompose the silver compound or complex, at least in part, to elemental silver in the presence of air. The dried particles may be gradually heated to a temperature not to exceed 500° C., preferably to a maximum in the range of about 300° to 400° C. and held at this temperature for a sufficient time to complete the activation, at which time the silver particle size will be 0.2-1.0 microns on the average and organic materials will have been substantially oxidized. This will generally require at least two hours at the maximum temperature.

It has been found important to activate the silver under conditions which produce the best activity if the post-deposition of alkali metals is to have its desired effect. While this statement might appear obvious, it is actually contrary to the teachings of the prior art, which would lead one skilled in the art to conclude that the activation should be so severe as to actually depress the catalyst performance. See for example U.S. Pat. No. 4,033,903 where the substantial increase in silver particle size is suggested to characterize the catalyst before alkali metals are added. However, according to the invention, activation of the silver can be carried out in the presence of molecular oxygen e.g. air and does not require an inert or reducing atmosphere. The temperatures should be regulated so that the silver particles are highly active and suitable for oxidation of ethylene to ethylene oxide so that the catalyst is suitable for use, even without the advantage obtained by post-deposition of an alkali metal(s). Preferably, the temperature will be raised gradually to a miximum in the range of 300°-400° C., and held at the maximum temperature for a period of about two hours, until the silver particles have reached the desired size and all organic materials have been removed. In a particularly preferred procedure, the impregnated support is heated to about 150° C., over two hours, then to about 200° C. over two hours, and finally to about 350° C. over two hours and held there for no more than two hours. The entire procedure does not exceed eight hours. Air will be passed over the silver-laden support during activation at at rate sufficient to assure oxygen is present at the surface of the support. Although air is the preferred gas, other gases may be used, provided they contain sufficient oxygen to oxidize the organic materials present.

The amount of alkali metal employed on the finished catalyst is generally similar to those employed heretofore. Thus, the amount deposited will be generally in the range of about 10–1000 ppm by weight, preferably about 25–500 ppm by weight, and particularly about 50–300 ppm by weight. The alkali metals of the periodic table include sodium, lithium, potassium, rubidium, and cesium. For purposes of the present invention, the latter three alkali metals are particularly preferred, especially cesium, although sodium and lithium are not necessarily excluded. The alkali metal(s) will be supplied as metal compound(s) which maybe associated with various anions, as for example hydroxide, nitrates, halides, formates, and acetates, particularly acetates. Conventiently, the alkali metal compounds are dissolved in water or alcohol-water solutions, and preferably ethanol.

Catalysts prepared by the procedures described above have improved performance for use in the production of ethylene oxide by the vapor phase oxidation of ethylene with of ethylene with molecular oxygen, as compared to catalyst containing only silver. Oxidation reaction conditions such as those previously known in the art may be employed. These usually involve reaction temperatures of about 150°–400° C., usually 200°–300° C., and reaction pressures in the range of from 0.5–35 kg/cm$^2$ gauge. Reactant feed mixtures usually contain 0.5–20% ethylene, 3–15% oxygen, with the balance comprising comparatively inert materials including such substances as nitrogen, carbon dioxide, methane, ethane, argon, and the like. Only a portion of the ethylene usually is reacted per pass over the catalyst and after separation of the desired ethylene oxide product and the removal of appropriate purge streams and carbon dioxide to prevent uncontrolled build-up of inerts and/or by-products, unreacted materials are returened to the oxidation reactor. The following examples will illustrate the preparation and use of catalysts according to the invention and will support those aspects previously disclosed as critical to achieving the desired results. Unless otherwise indicated, all parts and percentages are given by weight for liquids and solids, while for gases compositions are given as mol %, and flow rates are given in normal cubic meters per hour, i.e. at 0° C. and 760 mm Hg. The fraction of the ethylene converted to ethylene oxide is given as the percent selectivity, as is usual in the art.

EXAMPLE 1

The impregnating solution for the silver is prepared by dissolving 1633 gm of silver oxide in a solution of 580 gm of water in 2777 gm of lactic acid. The lactic acid-water solution is heated to 85° C. and 1633 gm of silver oxide is added in increments with vigorous stirring. Hydrogen peroxide is added to clear the solution of prematurely reduced silver followed by the addition of 17.8 gm of barium acetate dissolved in water. The support materisl (Norton 5552 ) is preheated to 85° C. and immersed in the solution for 20 minutes. The saturated support is drained and subjected to a programmed heat treatement in air to decompose organic residue and deposit silver metal in a form suitable for the finished catalyst. The heat program used is: 2 hours at 130° C., 2 hours at 200° C. and finally 2 hours at 350° C.

In order to transform the freshly activated silver catalyst into the finished catalyst a second impregnating solution of cesium acetate in a water-ethanol mixture is prepared. This solution is prepared by dissolving 34.4 gm of cesium acetate in 451 gm of distilled water. The resulting solution is mixed with 4049 gm of anhydrous ethanol. The resulting solution has 5287 ppm of $C_s$ in solution. The described impregnating solution is circulated through a bed of the activated silver catalyst for 2 hours. The excess solution is drained and the catalyst is subsequently washed with pure anhydrous ethanol. This step is repeated for a total of threee washes. The finished catalyst contains 15.0% Ag, 815 ppm Ba and 216 ppm Cs by analysis, with 88% selectively adsorbed.

A charge of 2460 gm of this catalyst as ¼" diameter rings is placed in a reactor consisting of an oil-jacketed vertical tube 21.8 mm internal diameter and a bed height 7.5 meters. A feed mixture of 0.2% ethane, 15ethylene, 7% oxygen, 6% carbon dioxide and 0.25 ppm ethylene dichloride and balance nitrogen was fed upward through the reactor at a GHSV of 6000 hr$^{31\ 1}$. The pressure was maintained at 17.6 kg/cm$^2$ gauge and temperature was maintained between 240–250° C.

TABLE 1

| Catalyst | Ag wt % | Cs ppm | Reactor Temp. °C. | % EO Outlet | % Sel. |
|---|---|---|---|---|---|
| 1 | 15 | 2.17 | 235 | 1.5 | 78.2 |

EXAMPLE 2

Catalysts are prepared by the method of Example 1 on supports of varying surface areas. Evelution of the catalysts is carried out as in Example 1 in a reactor consisting of a coiled stainless steel tube 5.33 mm internal diameter heated by a heat transfer medium of fluidized samd or molten salt. The catalysts are ground to 12-16 mesh and 36 gm having a bulk density of about 0.88 gm/cc is charged to the reactors. A feed mixture of 14% ethylene, 6.7% oxygen, 505% carbon dioxide and 0.25 ppm ethylene dichloride and balance nitrogen is passed over the catalyst. The gas hourly space velocity (GHSV) is 6000 hr[1] and temperature is maintained at 240-250° C. The results are shown in Table II.

TABLE II

| Catalyst | Support(1) | Support Surface Area m²/g | Reactor Temp. °C. | % Sel. |
|---|---|---|---|---|
| 2 | N5210 | 0.03 | 279 | 59.4 |
| 3 | N5551 | 0.2 | 249 | 74.5 |
| 4 | N5552 | 0.35 | 230 | 78.1 |
| 5 | N6847 | 0.59 | 220 | 79.7 |
| 6 | N3235 | 2.38 | 220 | 74.2 |

(1)Norton Company designations

EXAMPLE 3

A group of catalysts prepared accoprding to the method of Example 1 and tested according to the method of Example 2 show the effect of temperature of activation of the silver precursor. The results are shown in Table III.

TABLE III

| Catalyst | Temperature of Precursor Activation, °C. | Time of Activation hrs. | Reactor Temp. °C. | Sel. % |
|---|---|---|---|---|
| 7 | 350 | 2 | 232 | 76.3 |
| 8 | 350 | 16 | 244 | 76.1 |
| 9 | 400 | 2 | 233 | 76.6 |
| 10 | 500 | 2 | 235 | 75.7 |

EXAMPLE 4

A series of catalyst are prepared according to the procedure of Example 1 in which the cesium content is varied. The catalysts are tested according to the method of Example 2. The results are reported in Table IV, which shows that the silectivity to ethylene oxide improves with increasing amounts of cesium until after about 300 ppm the selectivity is lowered.

TABLE IV

| Catalyst | Silver Wt. % | Cesium ppm | Reactor Temp. °C. | Sel. % |
|---|---|---|---|---|
| 11 | 15 | 139 | 227 | 74.6 |
| 12 | 15 | 194 | 227 | 75.2 |
| 13 | 15 | 249 | 232 | 76.9 |
| 14 | 15 | 283 | 233 | 77.2 |
| 15 | 15 | 313 | 230 | 75.4 |
| 16 | 15 | 414 | 241 | 75.5 |
| 17 | 15 | 431 | 249 | 75.0 |

The beneficial effect of selective adsorption of the alkali metal on the support is illustrated in the following example.

EXAMPLE 5

An activated silver-containing support containing 15% silver by weight was prepared from Norton 5552 support according to the procedure of Example 1. For Catalyst 19, the finished catalyst was prepared by immersing the precursor in a solution of 679 ppm cesium acetate in 8% water 92% alcohol, draining and drying in a vacuum evaporator at 85° C. and 100 mm Hg. For catalyst 20, a 7024 ppm solution was circulated through the bed for 2 hours. The excess solution was drained and the catalyst was rinsed with three separate charges of pure anhydrous ethanol in an amount sufficient to cover the catalyst. The catalyst was dried in a vacuum evaporator at 85° C. and 100 mm Hg.

For catalyst 18, Norton 5210 support was used, which has a relatively lower capacity for selective adsorption of Cs. It contains about 86.9 wt % alumina and 11.6 wt% silica and has an apparent porosity of 40-45% and a surface area of 0.02-0.08 m²/g. About 20% of its pores are in the range of 1-10 microns, about 70% in the range of 10-100 mocrons, and about 10% above 100 microns. A 704 wt ppm cesium solution was circulated through the bed for 2 hours and after removed the catalyst as dried at 85° C. and 100 mm Hg pressure. The catalysts are tested by the methods of Example 2, with the results shown in Table V.

TABLE V

| Catalyst | Cesium Total Loading ppm | Cesium Selective Adsorption(1) % | Reactor Temp. °C. | % EO outlet | Sel. % |
|---|---|---|---|---|---|
| 18 | 164 | 32 | 279 | 1.50 | 59.4 |
| 19 | 270 | 61 | 242 | 1.50 | 76.2 |
| 20 | 212 | 85 | 232 | 1.50 | 77.0 |

(1)Calculated as = $\frac{\text{Total Cesium} - \text{Cesium calculated}}{\text{Total Cesium}}$ where:
Total Cesium = cesium on catalyst by atomic absorption analysis
Cesium calculated = cesium content calculated from amount and concentration of solution absorbed.

The invention claimed is:

1. A process for the oxidation of ethylene with molecular oxygen to ethylene oxide under oxidizing conditions employing an alkali metal-promoted supported silver catalyst suitable for the oxidation of ethylene to ethylene oxide prepared by the steps comprising:
   (a) impregnating a suport with a solution of an organic silver salt; said suport comprising alumina, silica, silica-alumina or combinations thereof having a surface area of about 0.1 to 1.0 m² and characterized by the ability to selectively adsorb an alkali metal in an amount greater than is calculated from the amount in a solution thereof which has been adsorbed;
   (b) separating the impregnated support of (a) from said solution and activating in the presence of molecular oxygen at a maximum temperature not exceeding 500° for a period of time sufficient to produce an active fresh silver catalyst having an average silver particle size of about 0.2-1.0 microns;
   (c) post-impregnating the active catalyst of (b) with a solution of a compound of at least on alkali metal selected from the group consisting of Cs, and Rb in an amount determined by the amount of alkali compound in solution or an excess of such amount, followed by washing off said excess with 1-3 carbon alkanol, and producing a finished catalyst containing 25-500 wt ppm of said alkali metal, whereby a substantial fraction of said alkali metal post-impregnated is selectively adsorbed.

2. The process according to claim 1 wherein said organic silver salt is silver acetate, silver oxalate, silver citrate, silver lactate, or silver benzoate.

3. The process according to claim 2 wherein said silver salt is silver lactate.

4. The process according to claim 3 wherein the maximum temperature of the activation is about 300-400° C.

5. The process according to claim 4 wherein the activation temperature does not exceed 350° C. and the time does not exceed eight hours total and two hours at the maximum temperature.

6. The process according to claim 1 wherein the maximum temperature of the activation is about 300-400° 1 C.

7. The process according to claim 6 wherein the activation temperature does not exceed not exceed 350° C. and the time does not exceed eight hours total and two hours at the maximum temperature.

8. The process according to claim 1 wherein the amount of alkali metal is determined by the amount of alkali compound in solution.

9. The process according to claim 1 wherein an excess of the amount of alkali compound in solution followed by washing off said excess with 1-3 carbon alkanol.

10. The process according to claim 1 wherein said alkali comprises cesium.

11. The process of oxidation according to claim 1 carried out temperatures in the range of about 150-400° C. at pressures in the range of 0.5-3.5 kg/cm$^2$ gauge.

12. The process according to claim 11 wherein ethylene is present in amounts in the range of 0.5 to 20% and oxygen is present in amounts in the range of 3-15%.

* * * * *